(12) United States Patent
Fischer, Jr.

(10) Patent No.: US 9,078,979 B2
(45) Date of Patent: Jul. 14, 2015

(54) CORKSCREW INJECTION NEEDLE

(75) Inventor: Frank J. Fischer, Jr., Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 42 days.

(21) Appl. No.: 13/142,496

(22) PCT Filed: Dec. 30, 2009

(86) PCT No.: PCT/US2009/069797
§ 371 (c)(1),
(2), (4) Date: Jun. 28, 2011

(87) PCT Pub. No.: WO2010/078409
PCT Pub. Date: Jul. 8, 2010

(65) Prior Publication Data
US 2011/0270199 A1    Nov. 3, 2011

Related U.S. Application Data

(60) Provisional application No. 61/141,545, filed on Dec. 30, 2008.

(51) Int. Cl.
*A61M 5/32* (2006.01)
*A61M 39/10* (2006.01)
*A61B 17/06* (2006.01)
*A61M 1/00* (2006.01)
*A61M 5/34* (2006.01)

(52) U.S. Cl.
CPC ...... *A61M 5/329* (2013.01); *A61B 2017/06076* (2013.01); *A61M 1/0064* (2013.01); *A61M 39/1055* (2013.01); *A61M 2005/341* (2013.01); *A61M 2039/1027* (2013.01); *A61M 2039/1033* (2013.01); *A61M 2039/1077* (2013.01)

(58) Field of Classification Search
CPC ............ A61M 5/329; A61M 39/1055; A61M 1/0064; A61M 2039/1027; A61M 2039/1033; A61M 2039/1077; A61B 2017/06076
USPC .......................... 604/272–274, 239, 533, 535
See application file for complete search history.

(56) References Cited

U.S. PATENT DOCUMENTS 5,405,376 A * 4/1995 Mulier et al. ................. 607/127
5,509,911 A * 4/1996 Cottone et al. ............... 604/536
(Continued)

FOREIGN PATENT DOCUMENTS

WO     WO 95/03843 A1     2/1995

*Primary Examiner* — Theodore Stigell
*Assistant Examiner* — Lauren M Peng
(74) *Attorney, Agent, or Firm* — Brinks Gilson & Lione

(57) ABSTRACT

An injection device including a syringe connectable to a corkscrew injection needle via an adapter is disclosed. The corkscrew needle includes a proximal end and a distal end and a bore formed through the proximal and distal ends, the corkscrew needle terminating with a sharpened tip at the distal end. The syringe includes a barrel and a chamber formed therein for containing an injectable substance. The barrel includes a proximal end, a distal end, and an outlet at the distal end in fluid communication with the chamber. The distal end of the syringe connects to the proximal end of the adapter. The adapter bore provides fluid communication between the syringe and the corkscrew needle. The proximal end of the corkscrew needle is rotatably coupled to distal end of the adapter which allows rotation of the corkscrew needle without rotating the syringe.

14 Claims, 3 Drawing Sheets

(56) References Cited

U.S. PATENT DOCUMENTS

| | | | |
|---|---|---|---|
| 5,620,421 A * | 4/1997 | Schmitz | 604/135 |
| 6,221,047 B1 * | 4/2001 | Greene et al. | 604/164.01 |
| 6,406,470 B1 * | 6/2002 | Kierce | 604/535 |
| 7,103,418 B2 * | 9/2006 | Laske et al. | 607/120 |
| 7,632,243 B2 * | 12/2009 | Bialecki et al. | 604/110 |
| 7,819,868 B2 * | 10/2010 | Cao et al. | 606/41 |
| 2005/0171474 A1 | 8/2005 | Mueller | |
| 2006/0036265 A1 * | 2/2006 | Dant | 606/144 |
| 2007/0198019 A1 * | 8/2007 | Schomer et al. | 606/79 |

\* cited by examiner

CORKSCREW INJECTION NEEDLE

CROSS-REFERENCE TO RELATED APPLICATIONS

This application is related to and claims the benefit of priority to PCT/US2009/069797, filed on Dec. 30, 2009 which claims priority to U.S. Provisional Patent Application Ser. No. 61/141,545, filed Dec. 30, 2008, entitled "CORKSCREW INJECTION NEEDLE," the entire contents of which are incorporated herein by reference.

BACKGROUND OF THE INVENTION

1. Field of Invention

The present invention relates to medical devices. More particularly, the invention relates to a medical injection device.

2. Background

Arteries carry blood rich in oxygen and nutrients from the heart to the rest of the body. As we age, a fatty material called plaque can build up in the walls of the arteries, causing them to narrow or become blocked, which can reduce or block blood flow. This condition is known as Peripheral Artery Disease (PAD) and most commonly affects blood flow to the legs.

Early symptoms of Peripheral Artery Disease include pain, cramping, or weakness in the legs when walking or climbing stairs, which may be relieved after resting. However, as plaque continues to build on the walls of the arteries in the legs, the symptoms of PAD can become more frequent and severe. In the advanced stages of PAD, blood flow to one or both legs can become severely limited. Severely blocked arteries in the leg and sharply diminished blood flow can result in wounds that do not heal, pain in the feet or legs, infections, and even gangrene. This painful condition is known as Critical Limb Ischemia (CLI), which may result in amputation.

Medical treatments including angioplasty, stents and bypass surgery may be implemented to repair blocked circulation in CLI patients' legs. A more recent medical treatment for CLI patients includes stem cell therapy. During the last several years, scientists have been studying the effects of using bone marrow cells to heal injured tissue. Bone marrow is the soft tissue within our bones. This tissue is home to unique cells commonly referred to as "adult stem cells." Stem cells are unique in that they can become many different types of cells. Other cells in our tissues, such as muscle cells or bone cells, can only divide to produce more muscle cells or bone cells (for example, muscle cells cannot become bone cells nor can bone cells become muscle cells). However, stem cells are different. These bone marrow stem cells can leave the bone and move through the arteries to an area of tissue injury. When stem cells arrive at an injury site, they respond to signals produced by the injured tissues and divide to generate other cell types. Stem cells can produce muscle cells, bone cells, or blood vessel cells, depending on what the body needs to repair itself. This process is believed to be of central importance in the body's attempt to repair the damage caused by PAD. It is thought that delivering these cells to the diseased tissue may improve blood flow and therefore, may improve the severe symptoms of Critical limb Ischemia.

In stem cell therapy, it is common to have multiple injection sites for injecting the stem cells into the patient's leg, for example, in order to build angiogenesis. To increase the volume of stem cells provided to the diseased tissue, there may be nearly one hundred needle injections about the lower leg. This is not only uncomfortable and painful for the patient, but requires an increased number of injection devices.

In view of the above, it is apparent that there exists a need for an improved medical injection device for stem cell therapy and other medical treatments.

BRIEF SUMMARY OF THE INVENTION

The present invention provides an improved medical injection device for embolic protection and an improved method of injecting an injectable substance into patient tissue.

In one embodiment, an injection device comprises a corkscrew injection needle and a syringe connectable to the corkscrew injection needle via an adapter. The corkscrew needle includes a proximal end and a distal end and a bore formed through the proximal and distal ends. The corkscrew needle includes a linear proximal portion and a spiral distal portion and terminates with a sharpened tip at the distal end for penetrating and advancing through patient tissue. In this embodiment, the adapter coupled to the corkscrew needle includes a proximal end and a distal end and an adapter bore formed through the proximal and distal ends. The distal end of the adapter is coupled to the proximal end of the corkscrew needle. In this embodiment, the syringe includes a barrel and a chamber formed therein for containing an injectable substance and plunger slidably disposed within the barrel. The barrel has a proximal end, a distal end, and an outlet at the distal end in fluid communication with the chamber. The distal end of the syringe connects to the proximal end of the adapter, the adapter bore providing fluid communication between the syringe and the corkscrew needle. The adapter allows rotation of the corkscrew needle without rotating the syringe.

In another embodiment, the injection device includes a syringe including a barrel having a chamber formed therein for containing an injectable substance and a plunger slidably disposed within the barrel. The barrel has a proximal end, a distal end, and an outlet at the distal end in fluid communication with the chamber. The injection device further includes a corkscrew injection needle connectable to the syringe for injecting the injectable substance into patient tissue. The corkscrew needle includes a proximal end and a distal end and a bore formed through the proximal and distal ends. The corkscrew needle terminates with a sharpened tip at the distal end for penetrating and advancing through the tissue. The corkscrew needle is connectable to the syringe via an adapter which allows rotation of the corkscrew needle without rotating the syringe.

The present invention further includes an improved method of injecting an injectable substance into patient tissue using an injection device in accordance with an embodiment described above. The method includes rotatably screwing the corkscrew needle into the tissue, connecting the syringe to the adapter coupled to the corkscrew needle, and rotatably unscrewing the corkscrew needle from within the tissue while simultaneously injecting the injectable substance into the tissue. In this embodiment, the adapter allows rotation of the corkscrew needle without rotating the syringe.

Further objects, features, and advantages of the present invention will become apparent from consideration of the following description and the appended claims when taken in connection with the accompanying drawings.

DETAILED DESCRIPTION OF THE INVENTION

The following provides a detailed description of currently preferred embodiments of the present invention. The description is not intended to limit the invention in any manner, but rather serves to enable those skilled in the art to make and use the invention.

Figure 1A:
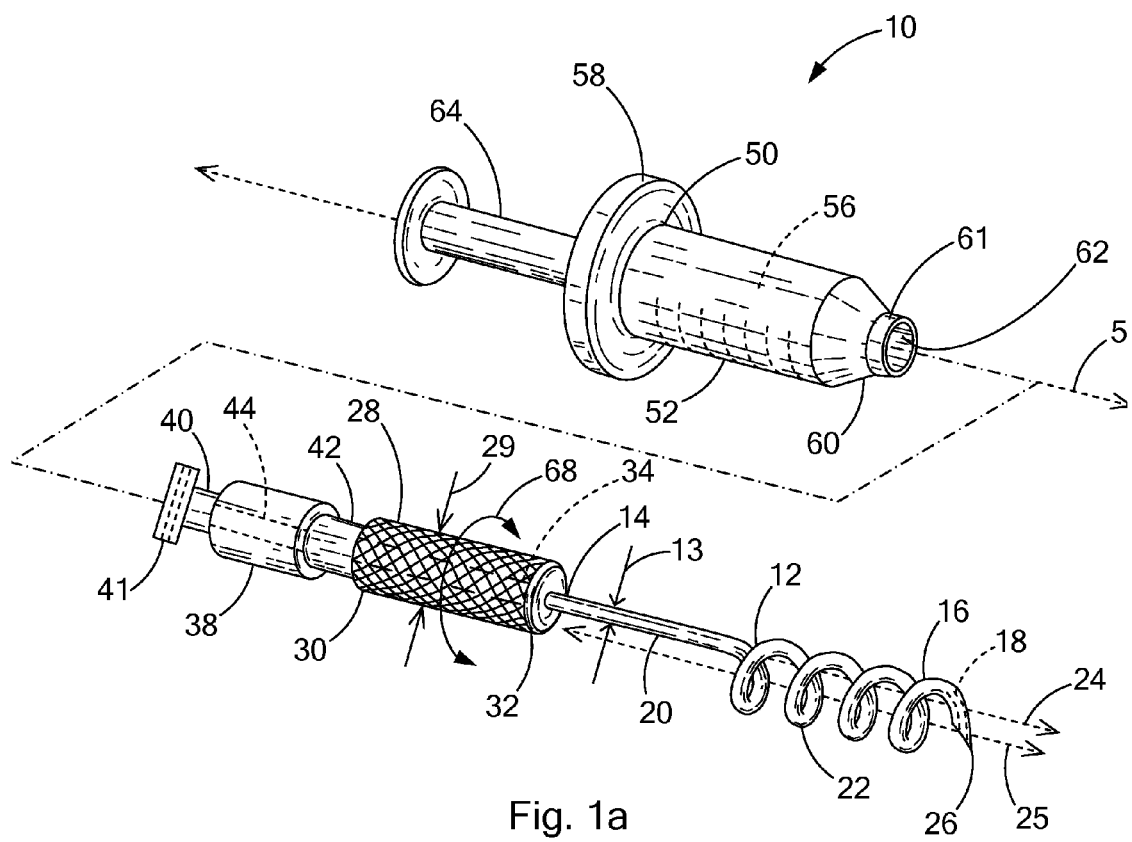
FIG. 1a is a perspective view of an injection device in accordance with an embodiment of the present invention.

Referring now to FIG. 1*a*, an injection device embodying the principles of the present invention is denoted by reference numeral 10. The device 10 includes a corkscrew injection needle 12 and an adapter 38 coupled to the corkscrew needle 12. The corkscrew needle 12 includes a proximal end 14 and a distal end 16 and a bore 18 formed through the proximal and distal ends 14, 16. As illustrated in FIG. 1, the corkscrew needle 12 includes a linear proximal portion 20 defining a longitudinal axis 24 and a spiral distal portion 22 extending distally from the linear proximal portion 20. In this embodiment, the spiral distal portion 22 extends distally from the linear proximal portion 20 in a helical or spiraled fashion to resemble a corkscrew, the spiral distal portion 22 being wound about a longitudinal axis 25 parallel to the longitudinal axis 24 defined by linear proximal portion 20. In one example, the longitudinal axes 24 and 25 may be the same such that the spiral distal portion 22 is wound about the longitudinal axis 24 defined by the linear proximal portion 20 (FIG. 1*b*).

Preferably, the linear proximal portion 20 extends proximally from the spiral distal portion 22 to a cylindrical needle hub 28 at the proximal end 14 of the corkscrew needle 12. In this embodiment, the needle hub 28 includes a proximal end 30 and a distal end 32 and a cavity 34 extending between the proximal and distal ends 30, 32. The distal end 32 is attached to the corkscrew needle 12 at the proximal end 14 of the corkscrew needle 12 by any suitable means known in the art, for example, via insert molding or gluing. It is also within the scope of the present invention for the corkscrew needle 12 to extend into the cavity 34. As shown in FIGS. 1*a-b* and FIG. 2, the corkscrew needle 12 has a first outer diameter 13 and the needle hub 28 has a second outer diameter 29 larger than the first outer diameter 13 of the corkscrew needle 12. The larger diameter needle hub 28 facilitates grasping and rotation of the corkscrew needle 12 during insertion into and withdrawal from patient tissue 36.

Figure 1B:
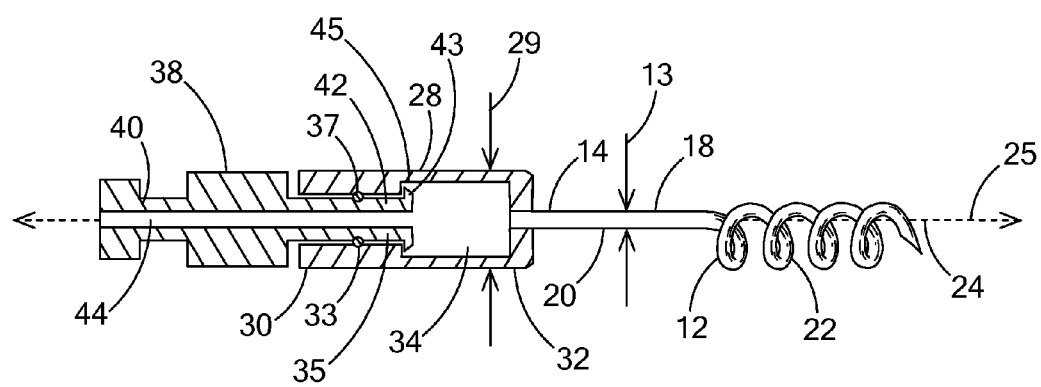
FIG. 1*b* is a partial side view, partly in cross-section, of an injection device in accordance with an embodiment of the present invention.
Figure 2:
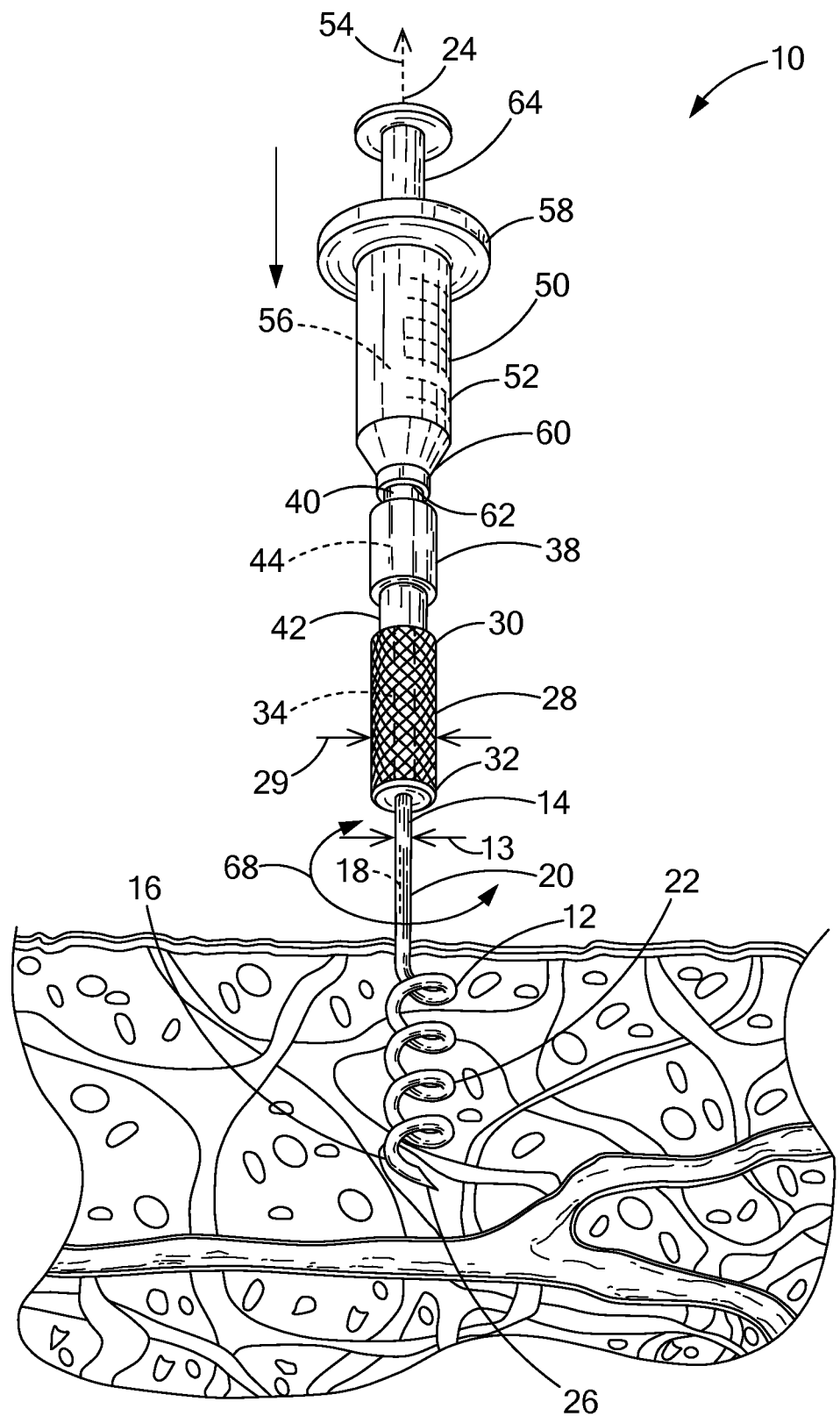
FIG. 2 is a perspective view of an injection device in accordance with an embodiment of the present invention advanced into patient tissue.

As illustrated in FIGS. 1*a-b* and FIG. 2, the injection device 10 further includes an adapter 38 coupled to the needle hub 28. The adapter 38 includes a proximal end 40 and a distal end 42 and an adapter bore 44 extending between the proximal and distal ends 40, 42. In this embodiment, a syringe 50 is connectable to the corkscrew needle 12 via the adapter 38. The syringe 50 includes a syringe barrel 52 having a longitudinal axis 54. The syringe barrel 52 includes a chamber 56 formed therein for housing an injectable substance. The syringe barrel 52 includes a proximal end 58 and a distal end 60 and an outlet 62 at the distal end 60 in fluid communication with the chamber 56. A plunger 64 is slidable within the syringe barrel 52 to dispense the injectable substance through the outlet 62 of the syringe 50.

Preferably, the chamber 56 houses stem cells for injection into the tissue of a patient's leg, for example, for the treatment of PAD. In another preferred embodiment, the chamber 56 houses extra cellular matrix (ECM) material, such as small intestine submucosa (SIS). SIS is a resorbable, acellular, naturally occurring tissue matrix composed of extracellular matrix (ECM) proteins in various growth factors. SIS is derived from the porcine jejunum and functions as a remolding bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. SIS has been shown to be completely replaced by the patient's own tissues over time. It is also within the scope of the present invention for the chamber 56 to contain any other suitable injectable substance for injection into patient tissue 36.

In a preferred embodiment, the distal end 42 of the adapter 38 is coupled to the proximal end 30 of the needle hub 28 via a fluid tight and rotatable fit such that the needle hub 28, and thus the corkscrew needle 12, is rotatable about the distal end 42 of the adapter 38 while maintaining a fluid tight seal between the adapter 38 and the needle hub 28. Referring to FIG. 1*b*, the distal end 42 of the adapter 38 includes an annular groove 35 and an annular ring 33, such as an o-ring, fitted within the annular groove 35. In this embodiment, the needle hub 28 includes an annular groove 37 formed within the proximal end 30 configured to receive the annular ring 33 of the adapter 38 to form a fluid tight and rotatable fit.

As illustrated in FIG. 1*b*, the distal end 42 of the adapter 38 preferably includes a flange portion 43 which abuts a shoulder 45 formed within the needle hub 28 to snap or lock the adapter 38 in place within the needle hub 28. In this embodiment, the flange portion 43 of the distal end 42 of the adapter 38 is collapsed or squeezed to fit through the proximal end 30 of the needle hub 28 which has a smaller inner diameter. Past a certain point within the cavity 34 of the needle hub 28, the inner diameter of the cavity 34 enlarges and the flange portion 43 of the distal end 42 of the adapter 38 expands to engage the shoulder 45 formed between the smaller and larger inner diameters within the cavity 34 of the needle hub 28. The flange portion 43 of the distal end 42 of the adapter 38 and the shoulder 45 formed within the cavity 34 of the needle hub 28 cooperate to lock the adapter 38 within the needle hub 28, however, the needle hub 28, and thus the corkscrew needle 12, is rotatable about the adapter 38 via the o-ring 33.

In this embodiment, the distal end 60 of the syringe 50 is configured for connection with the proximal end 40 of the adapter 38 via a luer fitting. For example, as illustrated in FIG. 1, the distal end 60 of the syringe 50 may include a male luer tip having male threads 61 and the proximal end 40 of the adapter 38 may include a female luer fitting having female threads 41 configured to receive the male threads 61 to form a fluid-tight, luer lock fit between the syringe 50 and the adapter 38. In FIG. 2, the syringe 50 and the proximal end 40 of the adapter 38 are connected via a luer fitting, however, the distal end 60 of the syringe 50 includes a female luer tip having female threads and the proximal end 40 of the adapter 38 includes a male luer fitting having male threads.

The proximal end 40 of the adapter 38 may connect to the distal end 60 of the syringe 50 and the distal end 42 of the adapter 38 may connect to the proximal end 30 of the needle hub 28 by any other suitable means known in the art which provides a fluid-tight fit between the syringe 50 and the corkscrew needle 12 and allows rotation of the corkscrew needle 12 into and out of patient tissue 36 without having to rotate the syringe 50.

When the syringe 50 is coupled to the adapter 38 the adapter bore 44 of the adapter 38 provides a fluid connection between the syringe 50 and the corkscrew needle 12. In this embodiment, the syringe chamber 56 is in fluid communication with the adapter bore 44, and the adapter bore 44 fluidly communicates with the cavity 34 within the needle hub 38, and the cavity 34 is in fluid communication with the needle bore 18. Thus, when the device 10 is fully assembled (i.e., the syringe 50 is connected to the adapter 38), the syringe 50 is in fluid communication with the corkscrew needle 12 for passage of the injectable substance contained within the syringe chamber 56 to the bore 18 of the corkscrew needle 12 during injection of the injectable substance into the patient tissue 36.

Figure 3:
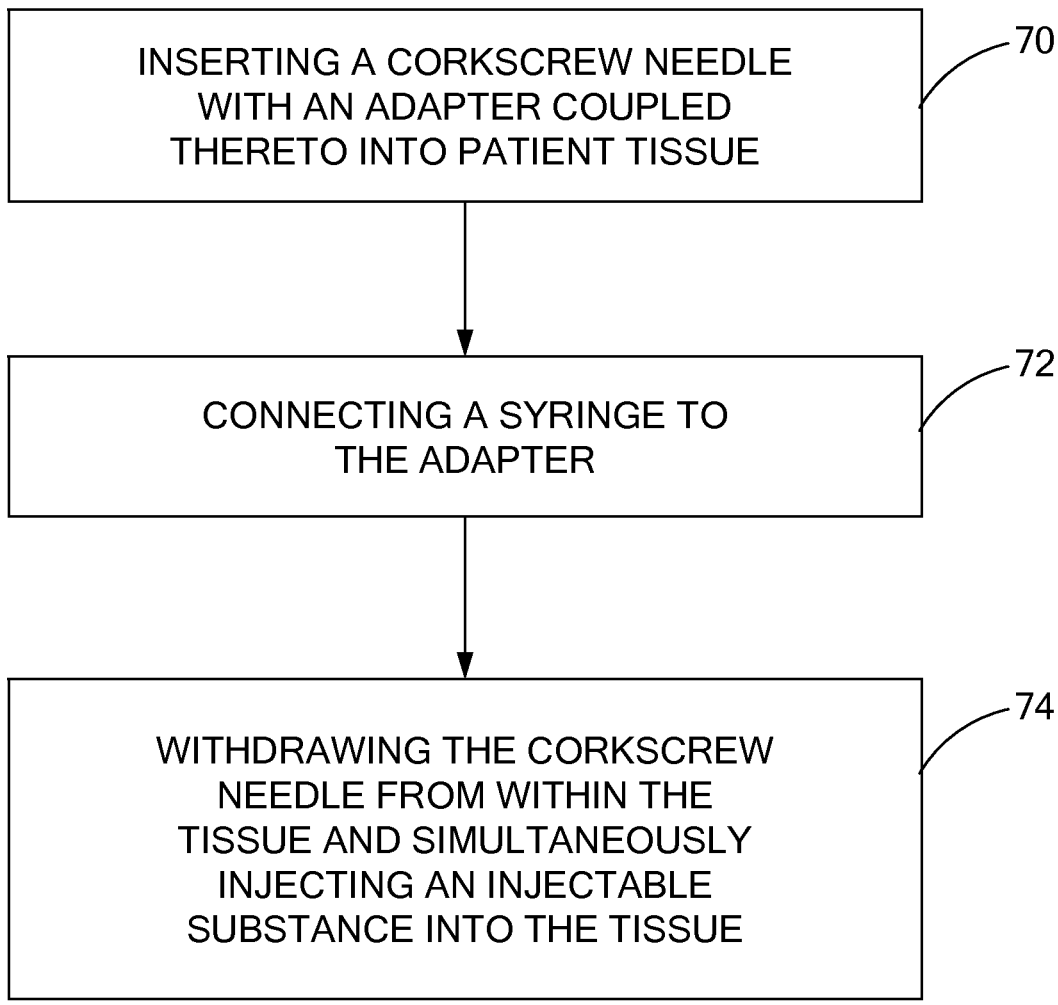
FIG. 3 is flow chart of a method of injecting an injectable substance into patient tissue.

Referring to FIG. 3, a method of injecting an injectable substance into patient tissue 36 is provided. Preferably, the method includes inserting (70) the corkscrew needle 12, with the adapter 38 attached thereto, into the patient tissue 36 prior to connection of the syringe 50 to the adapter 38. However, it is also within the scope of the present invention for the injection device 10 to be completely assembled (i.e., the syringe 50 connected to the corkscrew needle 12 via the adapter 38) prior to insertion of the corkscrew needle 12 into the patient tissue 36. Inserting (70) the corkscrew needle 12 into the patient tissue 36 includes rotatably screwing the corkscrew needle 12 into the patient tissue 36 as one would screw a corkscrew into a cork. This includes penetrating the patient tissue 36 with the sharp tip 26 at the distal end 16 of the corkscrew needle 12 and rotating the corkscrew needle 12 in a first direction about the longitudinal axis 24 while applying a distal force to the corkscrew needle 12. The corkscrew needle 12 is preferably rotated via grasping and turning the needle hub 28 about the longitudinal axis 24.

As the corkscrew needle 12 rotates, the sharp tip 26 penetrates deeper through the patient tissue 36, advancing the corkscrew needle 12 through the patient tissue 36 until at least the spiral distal portion 22 of the corkscrew needle 12 is inserted into the patient tissue 36. Compared to linear needle injection devices commonly used for injection of injectable substances into patient tissue 36, the corkscrew needle 12 provides a wider, longer tract through the patient tissue 36. The wider, longer tract is thus able to provide an increased volume of injectable substance to the patient tissue 36, substantially decreasing the number of injection sites and the number of injection devices needed for patients undergoing stem cell therapy for PAD, for example.

After the corkscrew needle 12 is properly inserted through the patient tissue 36, the method further includes aligning the longitudinal axes 54 and 24 of the syringe barrel 52 and the proximal linear portion 20 of the corkscrew needle 12, respectively, and connecting (72) the syringe 50 to the adapter 38, forming a completely assembled injection device 10. Once assembled, the corkscrew needle 12 is in fluid communication with the syringe chamber 56 via the adapter bore 44 and the cavity 34 within the needle hub 28.

The method further includes withdrawing (74) the corkscrew needle 12 from within the patient tissue 36 while simultaneously injecting (74) the injectable substance into the patient tissue 36. Withdrawing (74) the corkscrew needle 12 from the patient tissue 36 includes rotatably unscrewing and pulling the corkscrew needle 12 out from the patient tissue 36. This includes rotating the corkscrew needle 12 in a second direction about the longitudinal axes 24 and 54, the second direction opposite the first direction. The arrow 68 illustrates that the corkscrew needle 12 is rotatable 360 degrees about the longitudinal axes 24 and 54 in both the first and second directions.

In this embodiment, injecting (74) the injectable substance into the patient tissue 36 includes advancing the syringe plunger 64 from the proximal end 58 of the syringe barrel 52 toward the distal end 60 to dispense the injectable substance from the syringe 50 via the outlet 62. The injectable substance flows from the outlet 62 at the distal end 60 of the syringe 50 through the adapter bore 44 of the adapter 38, through the cavity 34 within the needle hub 28 and into the needle bore 18 of the corkscrew needle 12. The injectable substance travels through the needle bore 18 from the proximal end 14 of the corkscrew needle 12 through the linear proximal portion 20 and through the spiral distal portion 22, and exits the corkscrew needle 12 via an opening within the sharp tip 26 at the distal end 16 of the corkscrew needle 12.

In this embodiment, the rotatable fit between the needle hub 28 and the adapter 38 and the luer lock fit between the syringe 50 and the adapter 38 allows rotation of the corkscrew needle 12 as it is withdrawn or unscrewed from the patient tissue 36 without having to rotate the syringe 50. Thus, one hand is preferably used to rotate the corkscrew needle 12 via grasping and turning the needle hub 28 about coincident longitudinal axes 24 and 54 while the other hand is preferably used to distally advance the plunger 64 of the syringe 50 to inject the injectable substance through the device 10 and into the patient tissue 36.

Injecting (74) the injectable substance into the patient tissue 36 while simultaneously withdrawing (74) the corkscrew needle 12 provides the injectable substance to the patient tissue 36 throughout the length and width of the tract formed by the corkscrew needle 12. Thus, the injectable substance is more evenly diffused throughout the patient tissue 36 in comparison to providing a stream of just a single line of injectable substance as is the case with ordinary linear needle injection devices.

As a person skilled in the art will readily appreciate, the above description is meant as an illustration of the implementation of the principles of this invention. This description is not intended to limit the scope or application of this invention in that the invention is susceptible to modification variation and change, without departing from the spirit of this invention, as defined in the following claims.

The invention claimed is:

1. An injection device comprising:
 a corkscrew injection needle including a proximal end and a distal end and a needle bore formed through the proximal and distal ends, the corkscrew needle including a linear proximal portion and a spiral distal portion, the corkscrew needle terminating with a sharpened tip at the distal end for penetrating and advancing through patient tissue;
 a needle hub being permanently inseparably formed and being non-rotatably and permanently rigidly coupled to and surrounding a portion of the linear proximal portion;
 an adapter coupled to the needle hub, the adapter including a proximal end and a distal portion with a distal end and an adapter bore formed through the proximal and distal ends, the distal end of the adapter inserted into a proximal end of the needle hub and having an outward snap-in flange portion engaging an interior shoulder of the needle hub with a continuously rotatable, fluid-tight fit sealed with an annular ring between an exterior surface of the distal portion and an interior surface of the needle hub; and
 a syringe connectable to the corkscrew needle via the adapter, the syringe including a barrel and a chamber formed therein for containing an injectable substance and a plunger slidably disposed within the barrel, the barrel having a proximal end, a distal end, and an outlet at the distal end in fluid communication with the chamber, the distal end of the syringe connectable to the proximal end of the adapter, the adapter bore providing fluid communication between the syringe chamber and the needle bore, the adapter allowing rotation of the corkscrew needle without rotating the syringe.

2. The injection device of claim 1, wherein the distal end of the syringe is configured to connect to the proximal end of the adapter via a luer fit.

3. The injection device of claim 1, wherein the needle hub includes a cavity in fluid communication with the adapter bore and the needle bore.

4. The injection device of claim 3, wherein the distal end of the adapter and the proximal end of the needle hub include annular grooves and the annular ring fitted therein, the fluid-tight and rotatable fit remaining fluid-tight over a rotation of a plurality of revolutions of the needle hub relative to the adapter.

5. The injection device of claim 1, wherein the linear proximal portion of the corkscrew needle defines a first longitudinal axis, wherein the spiral distal portion of the corkscrew needle is spiraled about a second longitudinal axis parallel to the first longitudinal axis, and wherein the syringe barrel includes a third longitudinal axis which substantially coincides with the first longitudinal axis when the syringe is connected to the corkscrew needle via the adapter.

6. The injection device of claim 5, wherein the first and the second longitudinal axes are the same.

7. The injection device of claim 5, wherein the corkscrew needle is rotated about the first longitudinal axis in a first direction to rotatably screw the corkscrew needle into the tissue, wherein the corkscrew needle is rotated about the first longitudinal axis in a second direction opposite to the first direction to rotatably unscrew the corkscrew needle from within the tissue.

8. The injection device of claim 1, wherein the injectable substance includes one of stem cells and extra cellular matrix material.

9. An injection device comprising:
a syringe including a barrel having a chamber formed therein for containing an injectable substance and a plunger slidably disposed within the barrel, the barrel having a proximal end, a distal end, and an outlet at the distal end in fluid communication with the chamber; and
a corkscrew injection needle connectable to the syringe for injecting the injectable substance into patient tissue, the corkscrew needle including a proximal end and a distal end and a needle bore formed through the proximal and distal ends, the corkscrew needle terminating with a sharpened tip at the distal end for penetrating and advancing through the tissue,
a needle hub being permanently inseparably formed and being non-rotatably and permanently rigidly coupled to and surrounding the proximal end of the corkscrew needle;
the needle hub connectable to the syringe via an adapter rotatably inserted into a proximal end of the needle hub in a continuously rotatable and fluid-tight connection sealed with an annular ring, which allows rotation of the corkscrew needle without rotating the syringe, the fluid-tight connection remaining fluid-tight over a rotation of a plurality of revolutions of the corkscrew needle relative to the syringe, wherein the distal end of the adapter includes an outer annular groove and the proximal end of the needle hub includes an inner annular groove, and the annular ring is fitted in the annular grooves between the distal end of the adapter and the proximal end of the needle hub.

10. The injection device of claim 9, wherein the adapter includes an adapter bore formed through the proximal and distal ends providing fluid communication between the syringe and the corkscrew needle.

11. The injection device of claim 10, wherein the distal end of the syringe is configured to connect to the proximal end of the adapter via a luer fit.

12. The injection device of claim 10, wherein the needle hub includes a cavity in fluid communication with the adapter bore and the needle bore.

13. The injection device of claim 9, wherein the corkscrew injection needle includes a linear proximal portion defining a first longitudinal axis and a spiral distal portion wound about a second longitudinal axis parallel to the first longitudinal axis, and wherein the syringe barrel includes a third longitudinal axis which substantially coincides with the first longitudinal axis when corkscrew needle is connected to the syringe via the adapter.

14. The injection device of claim 13, wherein the first and the second longitudinal axes are the same.

* * * * *